United States Patent [19]
Bukosky et al.

[11] 4,149,231
[45] Apr. 10, 1979

[54] CAPACITANCE-TO-VOLTAGE TRANSFORMATION CIRCUIT

[75] Inventors: Allen A. Bukosky, Delavan; Paul P. Monroe, Janesville, both of Wis.

[73] Assignee: Bunker Ramo Corporation, Oak Brook, Ill.

[21] Appl. No.: 793,614

[22] Filed: May 4, 1977

[51] Int. Cl.² ............................................. H02M 7/00
[52] U.S. Cl. ................................ 363/59; 324/60 CD
[58] Field of Search ............ 320/1; 324/60 C, 60 CD, 324/61 R; 363/59, 60, 61, 178

[56] References Cited

U.S. PATENT DOCUMENTS

| | | | |
|---|---|---|---|
| 3,452,272 | 6/1969 | Collins et al. | 324/60 CD |
| 3,453,535 | 7/1969 | Anglin | 324/60 CD |
| 3,656,000 | 4/1972 | Neathery, Jr. | 324/60 CD |
| 3,886,447 | 5/1975 | Tanaka | 324/60 CD |
| 3,947,760 | 3/1976 | Noguchi et al. | 325/60 CD X |
| 4,001,676 | 1/1977 | Hile et al. | 324/60 CD |
| 4,040,041 | 8/1977 | Fletcher et al. | 324/60 CD X |

*Primary Examiner*—William M. Shoop
*Attorney, Agent, or Firm*—F. M. Arbuckle; J. Hoffman

[57] ABSTRACT

A capacitance-to-voltage transformation circuit for providing an output voltage proportional to capacitive variations includes a variable capacitor, a reference voltage source, and circuit means for charging the variable capacitor to the reference potential. A switch means alternately connects the variable capacitor to the charging means and to ground at a cyclical rate determined by an oscillator clock. An impedance means coupled between the charging and switch means, develops a voltage drop thereacross of a magnitude directly proportional to capacitance variations of the variable capacitor.

In accordance with another aspect of the invention, the circuit includes a compensating means for nullifying any fixed capacitance component of the variable capacitor.

12 Claims, 2 Drawing Figures

CAPACITANCE-TO-VOLTAGE TRANSFORMATION CIRCUIT

BACKGROUND OF THE INVENTION

The present invention is generally directed to a variable capacitance indicating circuit and more particularly to a capacitance-to-voltage transformation circuit which provides an output voltage having a magnitude directly proportional to variations in capacitance.

There are many applications where it is desirable, if not necessary, to be able to detect variations in capacitance. For example, in fluid level gauging, two plates are immersed in a fluid and a capacitance between the plates varies as the fluid level between the plates varies. Thus, fluid level may be determined by detecting the value of capacitance between the plates.

As another example, in pressure measuring systems, pressure-to-capacitance transducers have found wide acceptance because they characteristically provide a varying capacitance proportional to pressure variations. As the capacitance of the transducer is detected, the level of pressure may be determined.

These are but two examples of the many enrivonments in which the value of a capacitance is necessary information. In systems designed for detecting the value of a variable capacitance it is desirable to relate the value of capacitance in a readily useful form such as in a voltage having a magnitude directly related to variations in capacitance. The voltage may then be used as a control parameter or for deflecting a suitable meter movement for visually indicating the absolute value of the capacitance, or the absolute or relative variation in capacitance.

In order to provide an output voltage which varies linearly with capacitance changes, many capacitance-to-voltage transformation circuit schemes have been developed. However, the various circuits developed heretofore have all suffered from certain deficiencies which have limited their usefulness.

One variety of capacitance-to-voltage transformation circuit utilizes comparators or Schmitt triggers. Comparators and Schmitt triggers are characteristically sensitive to noise. Thus, such circuits are not suitable for use in environments where there is radiation from relays, ignition noise from automobiles for example or power supply lead noise. The noise generated by these sources would cause faulty operation of the comparators and Schmitt triggers and consequently result in improper detection of the capacitance values.

Another form of capacitance-to-voltage transformation circuit utilizes an oscillator which drives a diode bridge circuit. Such circuits are oscillator-amplitude sensitive and thus are not suitable for use in environments where there is poor supply voltage regulation. Even small variations in supply voltage, and thus small variations in oscillator amplitudes, greatly affects the capacitance value detection of such circuits.

Some variable capacitors, such as the pressure-to-capacitance transducers previously referred to, exhibit a fixed capacitance component and a variable capacitance component. When the value of the variable capacitance is of paramount importance, it is often desirable to cancel the fixed capacitance component to assure proper circuit operation. For example, in some circuit environments if the fixed capacitance component is not eliminated, the output voltage attributable to the fixed capacitance component may be excessively high. As a result, the gain of the capacitance-to-voltage transformation circuit must be reduced so that the circuit components will operate within acceptable and safe voltage limits. With the gain diminished, the ability to detect small changes in variable capacitance is substantially diminished.

It is therefore a general object of the present invention to provide a new and improved capacitance-to-voltage transformation circuit which provides an output voltage having a magnitude which is proportional to variations in capacitance.

It is another object of the present invention to provide a capacitance-to-voltage transformation circuit which is substantially insensitive to extraneous noise.

It is a further object of the present invention to provide a capacitance-to-voltage transformation circuit which is substantially insensitive to oscillator amplitude.

It is a still further object of the present invention to provide a capacitance-to-voltage transformation circuit which cancels the fixed capacitance component of a variable capacitor.

SUMMARY OF THE INVENTION

The invention provides a capacitance-to-voltage transformation circuit for providing an output voltage variation related to capacitance variations in a variable capacitor element comprising means for applying a reference voltage potential, circuit means coupled to the applying means for charging the variable capacitor element to the reference potential, switching means for cyclically connecting the variable capacitor element to the circuit means and to a ground potential, and impedance means coupled between the circuit means and the switching means for conducting the charging current provided by the circuit means to the variable capacitor during a predetermined portion of each of the switching cycles and for developing an output voltage variation related to the variations in capacitance of the variable capacitor.

BRIEF DESCRIPTION OF THE DRAWINGS

The features of the present invention which are believed to be novel are set forth with particularity in the appended claims. The invention, together with further objects and advantages thereof, may best be understood by reference to the following description taken in conjunction with the accompanying drawings, and in which:

DESCRIPTION OF THE PREFERRED EMBODIMENT

Figure 1:
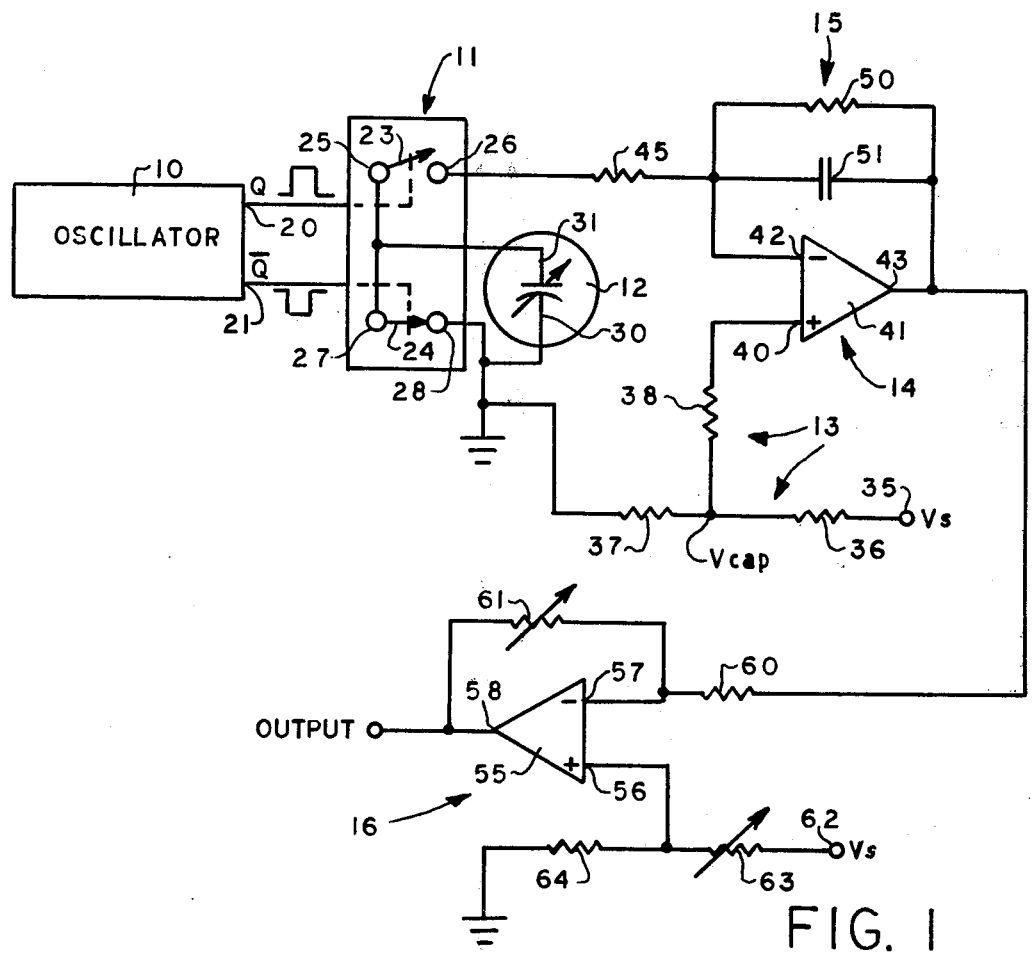
FIG. 1 is a schematic circuit diagram of a capacitance-to-voltage transformation circuit embodying the present invention.

Referring now to FIG. 1, there is illustrated in schematic form a preferred embodiment of a capacitance-to-voltage transformation circuit of the present invention. The circuit of FIG. 1 includes an oscillator 10, a switching means 11, a variable capacitor 12, a voltage source 13, a charging means 14, an impedance means 15, and an amplifier 16.

The oscillator 10 is depicted only in block form since its construction will be familiar to those skilled in the art from the discussion that follows. A pair of output leads 20 and 21 of oscillator 10 (which may be an astable multivibrator) generate a pair of square-wave output signals, these signals being of cyclically alternating opposite polarity with respect to an intermediate reference point. Thus, when output 20 is at a high level or a positive polarity, output 21 is at a low lever or negative polarity, and vice versa, as denoted in the drawing by the designations Q and $\overline{Q}$ and the square-wave signal waveforms depicted adjacent terminals 20 and 21, respectively. The frequency rate of oscillator 10 is selected to assure a full charging of the variable capacitance 12 on each charging cycle. The upper frequency limit of oscillator 10 is therefore dependent upon the recharging time constant of capacitor 12. The time constant is determined by the values of capacitor 12, resistor 45, and the internal resistance of switch 23. By way of example, the circuit of FIG. 1 will function properly at an oscillator frequency of 200 KHz with capacitor 12 being 10 picofarads, resistor 45 being in the range of 10 to 50 thousand ohms, and with the internal resistance of switch 23 being on the order of 100 ohms.

Switching means 11 comprises a pair of switches 23 and 24. Switch 23 is driven by the signal on output lead 20 of oscillator 10 and switch 24 is driven by the signal on output lead 21 of oscillator 10, as denoted by the dotted line extensions of leads 20 and 21 intercepting switches 23 and 24. Switches 23 and 24 are shown schematically as mechanical switch elements within the block outline 11 for convenience and clarity of illustration, but actually are comprised of well-known electronic switching combinations, such as field effect transistors or the like. The switches 23 and 24 open and close in alternation, as may be noted from the drawing, at a rate corresponding to the duration of the square-wave signals from oscillator 10. As can likewise be seen in the figure, switches 23 and 24 include terminals 25, 26 and 27, 28, respectively, with terminals 25 and 27 being coupled in common.

The variable capacitor 12 may comprise any of a wide variety of known variable, capacitance elements; for this embodiment, variable capacitor 12 is assumed to be a pressure-to-capacitance transducer. Capacitors of this kind normally include a dielectric substrate having on each opposed side thereof a planar metallic diaphragm element. As the pressure accross the diaphragms varies, the resulting capacitance between the parallel diaphragms also varies in a directly or linearly proportional relationship as may be measured at terminals connected to the opposed diaphragm elements. However, it will be recognized that in some instances, as where the indicator displaying measured capacitance is nonlinear, it may be desirable that capacitance 12 have a complementary nonlinear characteristic. A first terminal 30 of transducer 12 is preferably coupled in common to ground with the terminal 28 of switch 24. A second terminal 31 of capacitor 12 is coupled to the common connection of terminal 25 of switch 23 and terminal 27 of switch 24.

The reference voltage source 13 comprises a conventional DC supply voltage of positive polarity, denoted "$V_s$," at terminal 35, and resistors 36, 37 and 38. Resistors 36 and 37 are coupled in series from the V Supply to ground so as to form a voltage divider providing a preselected positive polarity reference potential at their common junction. The common junction of resistors 36 and 37 is coupled to the non-inverting input 40 of operational amplifier 41 by the resistor 38. Resistor 38 is provided to balance out any offset voltage which might be introduced by bias current flowing through unequal resistances at the inputs of operational amplifier 41.

The charging means 14 comprises the conventional operational amplifier 41 denoted in standard symbolic format in the drawing; amplifier 41 includes, in addition to input 40, an inverting input 42 and an output 43. Inverting input 42 is coupled to terminal 26 of switch by a resistor 45. The output 43 of operational amplifier 41 is also coupled to the inverting input 42 by impedance means 15 which comprises the parallel combination of a resistor 50 and a capacitor 51. As a result, resistors 45 and 50 and capacitor 51 are all coupled in common to the non-inverting input 42 of operational amplifier 41.

The amplifier 16 comprises a second conventional operational amplifier 55 which includes a non-inverting input 56, an inverting input 57, and an output 58. The output 43 of operational amplifier 41 is coupled to the inverting input 57 of operational amplifier 55 by a series resistor 60. The output 58 of the amplifier 55 is coupled to the inverting input 57 by a feedback resistor 61 that is selectively variable in magnitude.

The non-inverting input 56 is coupled to a source of reference potential available from the mid-point of a voltage divider network. Specifically, a selectively variable resistor 63 and a fixed resistor 64 are coupled in series between the V Supply and ground. Resistors 63 and 74 thus comprise an adjustable voltage divider network, the common junction of resistors 63, 64 being coupled to the non-inverting input 56 of operational amplifier 55 to provide an adjustable reference potential to this amplifier input.

In operation, oscillator 10 provides alternating opposite sense square-wave signals at output leads 20 and 21 at a frequency rate of, for example, 200 KHz. Because the signal output on lead 20 drives switch 23 and the output on lead 21 drives switch 24, switch 23 opens when switch 24 closes and vice versa. With switch 24 closed and switch 23 opened as shown, the first and second terminals 30, 31 of capacitor 12 are connected to ground potential. When switch 23 is closed and switch 24 is open, second terminal 31 of capacitor 12 will be coupled to the charging means 14 by resistor 45. Switches 23 and 24 are preferably configured to operate in a break-before-make mode. As a result, the second terminals 31 of variable capacitor 12 is cyclically connected to ground potential and to the charging means 14. Because output 43 of amplifier 41 is coupled to inverting input 42, the charging current supplied by output 43 will charge capacitor 12 to the reference potential at non-inverting input 40.

When capacitor 12 is grounded by the switching means 11, the capacitor 12 is fully discharged. When the switching means connects the variable capacitor 12 to the charging means it will conduct electrical charge of a magnitude indicative of its capacitance. The current to supply this electrical charge flows through resistor 50 of impedance means 15. The average charging current through resistor 50 results in an average voltage thereacross which appears at output 43 of operational amplifier 41 and constitutes an output voltage which is directly proportional to the capacitance of variable capacitor 12. As a result, the circuit of the present invention derives an output voltage that has a magnitude which is directly proportional to the capacitance of variable capacitor 12.

The capacitor 51 coupled across resistor 50 is selected of a value to suppress transient excursions in voltage that are not indicative of the value of variable capacitance 12. Capacitor 51 therefore eliminates voltage spikes and subsequent voltage decay which would otherwise appear across resistor 50 during intervals when capacitor 12 is coupled to ground. Capacitor 51, in other words, integrates the voltage across resistor 50 to provide an average voltage which has a magnitude proportional to the capacitance of variable capacitor 12.

The voltage at output 43 is amplified by operational amplifier 41 to provide a second output voltage at output 58 which comprises the output voltage at output 43 of operational amplifier 41 amplified by a given factor. Amplifier 16 includes variable resistors 61 and 63 which comprise adjustable circuit means for selectively adjusting the slope of the second output voltage with capacitance variations and the zero intercept of the second output voltage. Specifically, resistor 61 by being coupled across the inverting input 57 and the output 58 provides a variable gain for operational amplifier 55. As resistor 61 is varied, the slope of the second output voltage-to-capacitance variations relationship changes.

Variable resistor 63 is adjustable for providing an adjustable reference potential at non-inverting input 56. As variable resistor 60 is varied, the zero intercept of the second output voltage is varied. Variable resistor 63 therefore provides a convenient means when output 58 is coupled to a meter and wherein it is desired that the meter read zero when the variable capacitance component of variable capacitor 12 is zero.

Figure 2:
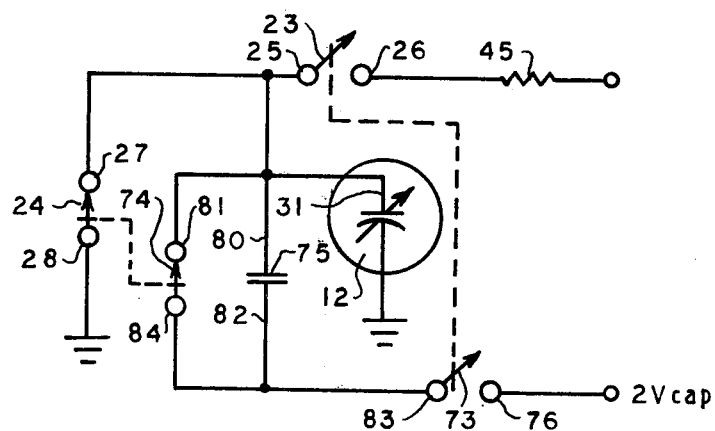
FIG. 2 is a schematic circuit diagram of a compensating means for cancelling the fixed capacitance component of a variable capacitor to be measured, in accordance with another aspect of the present invention.

Referring now to FIG. 2, there is shown a compensating means in accordance with the invention which may be utilized for eliminating or offsetting the fixed capacitance component of variable capacitor 12. The compensating means comprises a second switching means which includes switches 73 and 74, a fixed capacitor 75, and a second voltage source applied to terminal 76 of switch 73. Switches 73 and 74, likewise shown schematically as mechanical switch elements, open and close in synchronism with switches 23 and 24, respectively. Switch 73 therefore may be controlled by the output on lead 20 of oscillator 10 of FIG. 1 and switch 74 may be controlled by the output on lead 21 of oscillator 10 of FIG. 1.

Fixed capacitor 75 is preferably chosen to have a value equal to the amount of capacitance comprising the fixed capacitance component of variable capacitor 12. In a similar manner, the second DC voltage source coupled to terminal 76 of switch 73 is preferably chosen to have a voltage potential which is twice the reference potential applied to the input 40 of operational amplifier 41. Capacitor 75 has a first terminal 80 which is coupled in common to the second terminal 31 of variable capacitor 12, a terminal 81 of switch 74, the terminal 25 of switch 23, and the terminal 27 of switch 24. A second terminal 82 of capacitor 75 is coupled to a terminal 83 of switch 73 and to a terminal 84 of switch 74.

As in the embodiment of FIG. 1, switch 24 has a second terminal 28 coupled directly to ground and switch 23 has a terminal 26 coupled to resistor 45. Resistor 45 may in turn be coupled to the inverting input 42 of operational amplifier 41 of FIG. 1. All of the circuitry following resistor 45 may be the same circuitry as shown in FIG. 1 in practicing this embodiment of the present invention.

Because switches 73 and 74 open and close in synchronism with switches 23 and 24, the second terminal 82 of capacitor 75 is cyclically connected to the second voltage source when the variable capacitor 12 is connected to the charging means and to the first terminal 80 and hence to ground when the variable capacitor 12 is connected to ground potential. In other words, the second terminal 82 of capacitor 74 is coupled to the second voltage source when switch 73 is closed and switch 74 is open, and is coupled to its first terminal 80 and hence to ground in parallel with the variable capacitor 12 when switch 74 is closed and switch 73 is open. Switches 73 and 74 like switches 23 and 24 are preferably of the type which operate in the break-before-make mode.

The circuit of FIG. 2 enables the fixed capacitance component of variable capacitor 12 to be effectively cancelled and its effect on the output voltage nullified. With capacitor 75 being charged to the voltage at terminal 76, which voltage is equal to twice the reference potential applied to the noninverting input 40 of operational amplifier 41, an average current is introduced at the input 40 which is opposite to that introduced by the fixed capacitance component of variable capacitor 12. As a result of the opposed current and the resultant cancellation of the fixed capacitor component, the operational amplifiers 41 and 55 of FIG. 1 may be operated at an optimum gain because an excessive output voltage component attributable to the fixed capacitance component will not be present. Also, this reduced the requirements on the input offset drift and power supply rejection ratio of operational amplifier 55 as will be understood by those skilled in the art. Because the operational amplifiers may be operated at their optimum gain, very small variations in capacitances may more easily be detected.

As a further modification, capacitor 75 of FIG. 2 may be a variable capacitor similar to capacitor 12. In this case, the voltage developed at output 58 (FIG. 1) will have a magnitude which is related to the capacitance differential between capacitor 12 and capacitor 75. If capacitors 12 and 75 are both pressure-to-capacitance transducers, the output voltage will indicate the difference in pressure between the pressure on capacitor 12 and the pressure on capacitor 75.

The capacitance-to-voltage transformation circuit of the present invention is insensitive to noise because no comparators or Schmitt triggers are utilized. Also, because one side of the variable capacitor is coupled to ground, one-half of the variable capacitor shields the other half from extraneous noise also reducing the noise sensitivity of the circuit. The capacitance-to-voltage transformation circuit of the present invention is also insensitive to oscillator amplitude inasmuch as the oscillator signals only need open and close switches 23, 24, and switches 73, 74 when the compensating means is utilized. Because the circuit of the invention exhibits insensitivity to noise and oscillator amplitude variations, it will be recognized that it is suitable for detecting variations in capacitance in most any environment.

While particular embodiments of the present invention have been shown and described, modifications may be made, and it is therefore intended to cover in the appended claims all such modifications which fall within the true spirit and scope of the invention.

We claim:

1. A capacitance-to-voltage transformation circuit for providing an output voltage variation related to capacitance variations in a variable capacitor element, comprising:

means for applying a reference voltage potential;

circuit means coupled to said applying means for charging said variable capacitor element to said reference potential;

switching means for cyclically connecting said variable capacitor element to said circuit means and to a ground potential; and impedance means coupled between said circuit means and said switching means for conducting the charging current provided by said circuit means to said variable capacitor during a predetermined portion of each of said switching cycles and for developing an output voltage variation related to the variations in capacitance of said variable capacitor.

2. A capacitance-to-voltage transformation circuit as defined in claim 1 wherein said variable capacitor comprises a pressure-to-capacitance transducer.

3. A capacitance-to-voltage transformation circuit as defined in claim 1 said circuit means comprises a first operational amplifier having an output coupled to one side of said impedance means, a non-inverting input coupled to said applying means, and an inverting input coupled to the other side of said impedance means.

4. A capacitance-to-voltage transformation circuit as defined in claim 1 further including an oscillator coupled to said switching means for causing said switching means to cyclically connect said variable capacitor to said circuit means and to a ground potential.

5. A capacitance-to-voltage transformation circuit as defined in claim 1 in which said impedance means includes a fixed capacitor for suppressing transient changes in said output voltage which are not representative of capacitive variations.

6. A capacitive-to-voltage transformation circuit as defined in claim 1 and further including an operational amplifier having an input coupled to said impedance means and an output for providing a second output voltage which comprises said impedance means output voltage amplified by a given factor.

7. A capacitance-to-voltage transformation circuit as defined in claim 6 wherein said second operational amplifier includes adjustable circuit means for selectively adjusting both the slope of said second output voltage with capacitance variations and the zero intercept of said second output voltage.

8. A capacitance-to-voltage transformation circuit in accordance with claim 1 wherein said variable capacitor has both a fixed capacitance component and a variable capacitance component, and wherein said circuit also includes compensating means for effectively cancelling said fixed capacitance component.

9. A capacitance-to-voltage transformation circuit as defined in claim 8 wherein said compensating means includes a fixed capacitor having a first side coupled to said variable capacitor, means for applying a second reference voltage, and second switching means, and wherein said second switching means cyclically connects the other side of said fixed capacitor to said second voltage applying means when said variable capacitor is connected to said circuit means and to said first side when said variable capacitor is connected to ground potential.

10. A capacitance-to-voltage transformation circuit as defined in claim 9 wherein the capacitance of said fixed capacitor is equal to said fixed capacitance component and wherein said second applying means provides a voltage which is twice said reference potential.

11. A capacitance-to-voltage transformation circuit as defined in claim 1 further including a second variable capacitance having a first side coupled to said variable capacitor element, means for applying a second reference voltage, and second switching means, said second switching means cyclically connecting the other side of said second variable capacitor to said second voltage applying means when said variable capacitor element is connected to said circuit means and to said first side when said variable capacitor is connected to ground potential.

12. A capacitance-to-voltage transformation circuit for providing an output voltage variation which is directly proportional to variations in capacitance comprising:

a variable capacitor having first and second terminals, said first terminal being coupled to ground potential, and characterized by a fixed capacitance component and a variable capacitance component;

first means for applying a first reference voltage potential;

circuit means coupled to said applying means for charging said variable capacitor to said reference potential;

first switch means for cyclically connecting said second terminal to said circuit means and to ground potential;

a fixed capacitor having first and second terminals, said first terminal being coupled to said variable capacitor second terminal;

second means for applying a second reference voltage potential;

second switching means operating in synchronism with said first switching means for cyclically connecting said fixed capacitor second terminal to said second voltage source when said variable capacitor second terminal is connected to said charging means, and to said variable capacitor second terminal when said variable capacitor second terminal is connected to ground potential to effectively cancel said fixed capacitance component of said variable capacitor; and impedance means coupled between said circuit means and said first and second switching means for conducting the charging current provided by said circuit means to said variable capacitor during each said switching cycle and for providing an output voltage which is directly proportional to the variations in capacitance of said variable component of said variable capacitor.

* * * * *